United States Patent [19]

Barberet-Maiolino et al.

[11] Patent Number: Plant 7,300

[45] Date of Patent: Aug. 21, 1990

[54] STANDARD CARNATION NAMED LONTILTO

[75] Inventors: Nicole Barberet-Maiolino; Henri Blanc, both of Antibes, France

[73] Assignee: Laboratorie de Physiologie Vegetale, La Londe-les-Maures, France

[21] Appl. No.: 255,443

[22] Filed: Oct. 11, 1988

[51] Int. Cl.[5] ..... A01H 5/00

[52] U.S. Cl. ..... Plt./71

[58] Field of Search ..... Plt. 71

*Primary Examiner*—James R. Feyrer

*Attorney, Agent, or Firm*—Charles W. Rummler

[57] ABSTRACT

A new standard carnation variety particularly distinguished by the Empire Rose coloration of its medium sized flowers, which are borne singly on long, strong stems and produced profusely on a tall plant having a recurrent blooming habit, which flowers during the Spring, midseason and Fall blooming periods, the plant having a vigorous, upright and rather rigid growth habit with strong stems and a moderately abundant quantity of foliage, as well as being very resistant to Fusarium Oxysporum.

1 Drawing Sheet

BACKGROUND OF THE NEW PLANT

This new carnation cultivar originated as a seedling of a hybrid developed by us by crossing selected varieties of carnation plants from our collection of plants maintained for breeding purposes with the object of producing new plants of good quality, good flower production and color, and having a strong resistance to Fusarium Oxysporum. This breeding was done by us at our nursery at 83250 La Londe-Les-Maures, France, and from the resulting seedlings, we selected the present plant for propagation because of its apparently excellent growth habit and its profuse production of medium sized blooms having a very attractive coloration. Propagation of this selected seedling was done by us and under our direction at La Londe by means of cuttings of the original plant and with such success that we determined that further propagation would be worthwhile. That was done by means of cuttings from successive generations, as well as in vitro propagation procedures, which demonstrated conclusively that from generation to generation the original characteristics of the selected seedling were fully maintained and the homogeneity of the new plant could be assured. Propagation of this new plant is now being carried on at La Londe for commercial purposes by means of in vitro propagation, as well as by cuttings.

DESCRIPTION OF THE DRAWING

Our new carnation cultivar is illustrated by the accompanying photographic drawing, which shows several stems with buds and blooms including a three-quarter face view of a mature flower, the color rendition being as nearly true to that herein specified as is reasonably possible to obtain by professional photographic procedures.

DESCRIPTION OF THE NEW PLANT

The following is a detailed description of our new carnation variety based upon observation of plants grown under glass as well as outdoors at our La Londe nursery, the color designations being according to The R.H.S. Colour Chart published by The Royal Horticultural Society of London, England.

THE PLANT

Origin: Seedling.

Parentage:

*Seed parent.*—Variety No. 81 R 21 (unpatented).

*Pollen parent.*—Variety No. 9652 R (unpatented). The selected varieties are identified in our breeding records maintained at our La Londe nursery.

Classificaton:

*Botanic.*—*Dianthus Caryophyllus.*

*Commercial.*—Standard carnation.

Form: An erect bush aving at least four stems emitted near the ground.

Height: Averages about 115 cm. at eight months.

Main stem length: Less than 15 cm. due to pinching.

Branching character: Moderate.

Growth: Vigorous, upright and rather rigid.

Foliage:

*Quantity.*—Moderately abundant.

*Number of leaves.*—More than 120.

*Leaf size.*—About 14.8 cm. long and about 1.3 cm. wide at the seventh node.

*Leaf shape.*—Oblong with curved and entire margins.

*Texture.*—Leathery.

*Ribs and veins.*—Hardly noticeable.

*Rachis.*—Hardly noticeable.

*Color.*—Upper side, 189-A/189B. Under side, 189-A/189B.

*Leaflets.*—none.

THE BUD

Size: Medium.

*Diameter.*—Averages about 2.1 cm.

*Length.*—Averages about 2.5 cm.

Shape: Globular.

Rate of opening: Normal.

Color of petals: When sepals first divide, 49-B. When petals begin to unfurl, 48-D.

Sepals:

*Number.*—Five.

*Shape.*—Generally ovate but joined together at the lower part and terminating with an acuminate apex.

*Character.*—The sepals are hooded over the bud but curl back when the flowers open.

*Color.*—Inside, 145-D. Outside, 145-A/143-C.

Calyx:

*Shape.*—Somewhat splayed.

*Size.*—Large.

*Splitting.*—The calyx does split a little.

*Aspect.*—Smooth.

Flower stem:

*Character.*—Erect and rather rigid.

*Color.*—189-A/189-B.

THE FLOWER

Blooming habit: Reccurrent and profusely during Spring, midseason and Fall blooming periods.

Flower size: Medium.

*Diameter.*—Averages about 8.5 cm.

*Depth.*—Averages about 6 cm.

Borne: Singly on a stout and rigid upright stem.

Shape: When bloom first opens, high centered. When bloom matures, ball-shaped.

Petalage:

*Number of petals.*—Averages about eighty-seven.

*Arrangement.*—Imbricated.

*Form.*—Fan-shaped with very rounded edges and serrated apex.

*Texture.*—Leathery.

*Aspect.*—Satiny.

*Color.*—Outer petals and inside petals: Body — Empire Rose 48-D. Base — Greenish White. Reverse side — Venetian Pink 49-B.

*Petaloids.*—Number: Less than nine. Size: Smaller than the petals. Color: The same as the petals.

Flower stem:

*Length.*—Averages about 79.5 cm. cut at the tenth node.

*Character.*—Upright with very good strength.

*Color.*—189-A/189-B.

Persistence: The flowers hang on and dry.

Fragrance: Perceptible.

Disease resistance: Very resistant to *Fusarium oxysporum* as observed I.N.R A. 06600 Antibes. France.

Lasting quality: At least ten days as a cut flower in vase keeping.

REPRODUCTIVE ORGANS

Stamens:

*Number.*—Seven to ten.

*Arrangement.*—Encircling the ovary.

*Anthers.*—Size: About 4 mm. Color: Whitish.

Pistils:

*Number.*—Two to four.

*Number.*—Two to four.

*Styles.*—Length: Averages about 2.2 cm. Color: Slightly tinged with pink.

*Stigmas.*—Color Slightly tinged with pink.

Character of ovaries: Ribbed.

This new carnation variety most nearly resembles the variety 'Londaxie' (U.S. Pat. No. P.P. 5,530) but differs in color, lack of color defects, and has a thicker, more substantial stem.

We claim:

1. The new and distinct carnation cultivar substantially as herein shown and described, particularly distinguished by the Empire Rose coloring of its medium sized and well formed flowers borne singly on strong, upright stems on a plant having a vigorous and rather rigid growth habit and moderately abundant foliage.

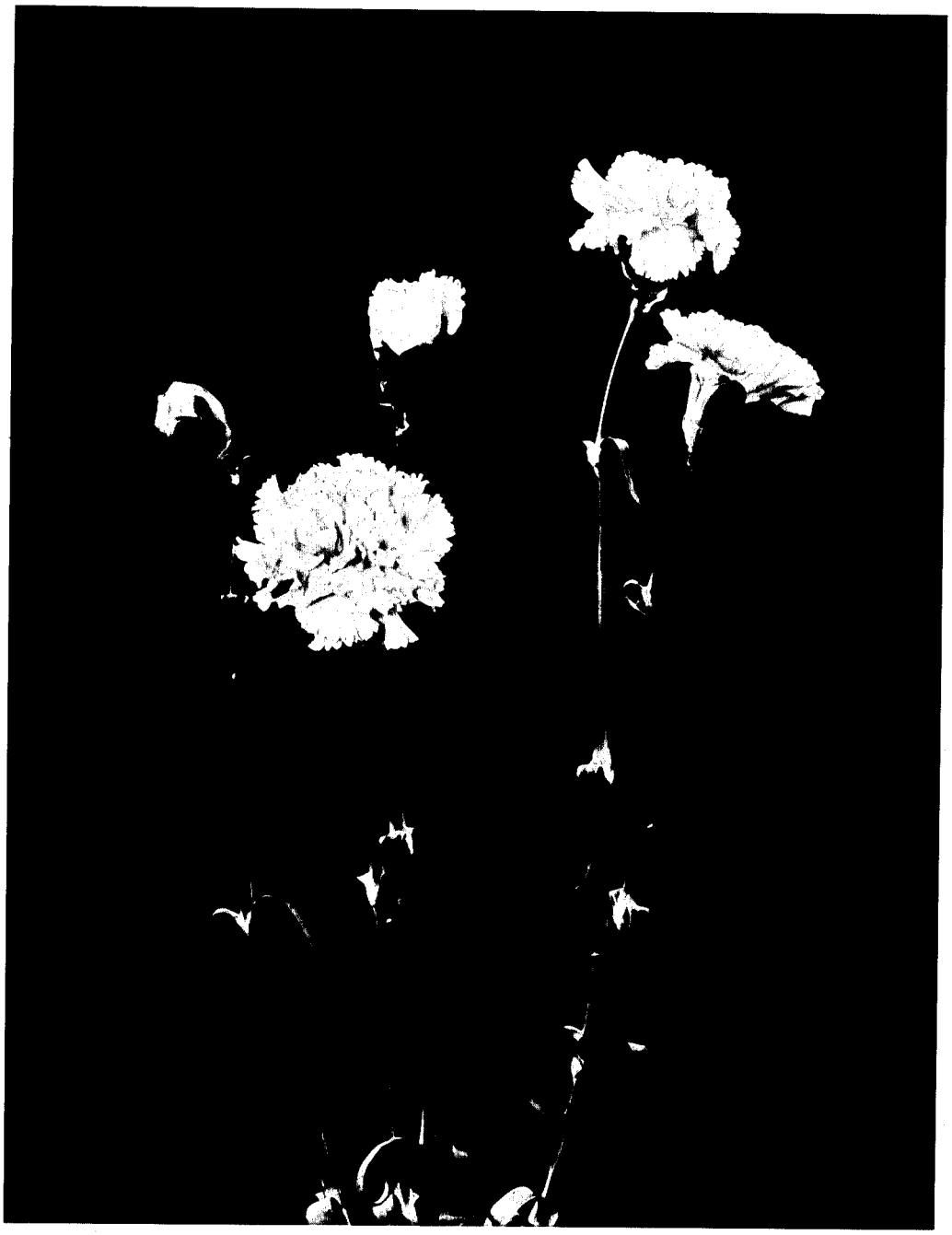

* * * * *